United States Patent [19]

Le Sonn

[11] 4,417,357

[45] Nov. 22, 1983

[54] SPACE-SAVING SELECTOR

[75] Inventor: Marcel Le Sonn, Paris, France

[73] Assignee: Thomson-CSF, Paris, France

[21] Appl. No.: 384,750

[22] Filed: Jun. 3, 1982

[30] Foreign Application Priority Data

Jun. 5, 1981 [FR] France .............................. 81 11222

[51] Int. Cl.³ ............................................ G03B 41/18
[52] U.S. Cl. .................................... 378/177; 378/176
[58] Field of Search ........................ 378/176, 177, 167

[56] References Cited

U.S. PATENT DOCUMENTS

| | | | |
|---|---|---|---|
| 2,832,893 | 4/1958 | Camardella | 378/177 |
| 3,624,398 | 11/1971 | Arndt | 378/177 |
| 3,710,106 | 1/1973 | Loucheur | 378/176 |
| 3,936,642 | 2/1976 | Lajus et al. | 378/177 |

FOREIGN PATENT DOCUMENTS 1033830  6/1966  United Kingdom ................ 378/176

Primary Examiner—Alfred E. Smith
Assistant Examiner—T. N. Grigsby
Attorney, Agent, or Firm—Cushman, Darby & Cushman

[57] ABSTRACT

A space-saving selector is provided for equipping radiological apparatus.

The selector of the invention equipping a radiological examination table is operational for radiography in all the positions which it occupies in the table, including the endmost positions.

Such a selector may equip any radiological apparatus comprising a radiographic film capable of being alternately sensitized and protected.

10 Claims, 1 Drawing Figure

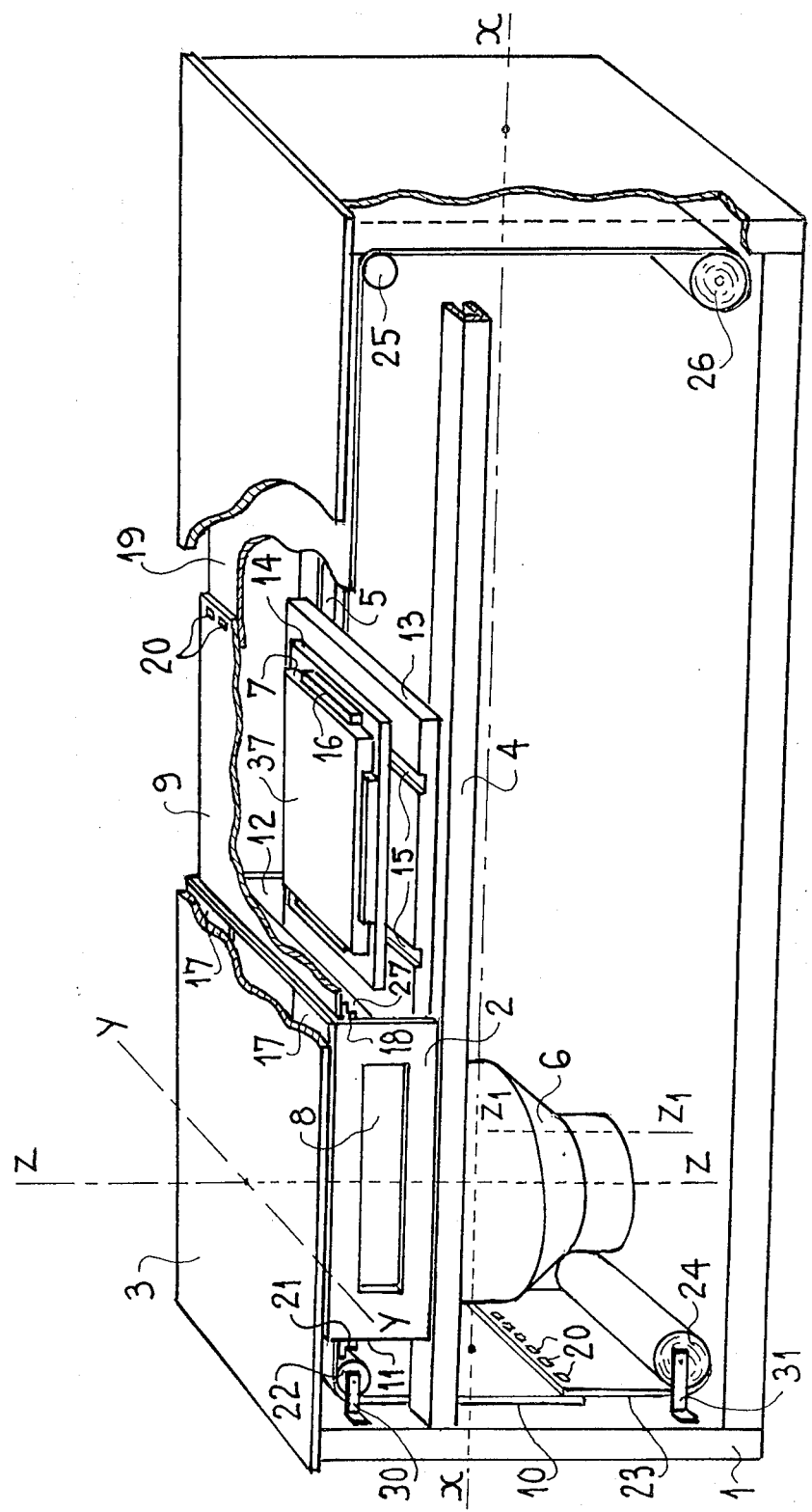

SPACE-SAVING SELECTOR

BACKGROUND OF THE INVENTION

The present invention relates to a space-saving selector for equiping radiological apparatus.

The different radiological stands, and more especially conventional stands with remote-controlled tables, comprise a selector. This latter, located in the examination table under the patient-carrying panel, is meant to receive a cassette containing a radiographic film for providing radiograms of the desired format. Generally, for this purpose, the cassette moves in the selector under an adjustable masking device, such for example as mobile masking flaps: the movements of said cassette and masking flaps are controlled by electro-mechanical or electronic means which this selector comprises, so as to cause the cassette to occupy a position in which the exposed radiographic film surface corresponds to the desired format.

A radioscopic examination is frequently carried out before the virtual radiological image is fixed on the radiographic film and a radiation detector such as a luminance amplifier is then used. This latter, as well as the selector, is able to move inside the examination table along an axis parallel to the longitudinal axis thereof and, by means of a servo-control device, the position of the selector may be centered on that of the luminance amplifier. Thus, after the radioscopic examination, the radiography may be undertaken with a minimum loss of time, since the selector is already in the proper position: of course, during the radioscopy, the path must be freed for the radiation beam, more especially by moving aside the masking flaps and the cassette.

So, there exist selectors in which the radiographic cassette, during the radioscopy sequence, is sheltered from the X-rays in a waiting position, in an additional space which this selector comprises; but this requires a larger dimension of this latter which must then comprise at least one surface double that of the radiographic cassette. This dimensional increase of the selector is provided either along the longitudinal axis of the examination table or along the transverse axis thereof.

The disadvantages thereof are the following: in so far as the increase in the dimension of the selector along a longitudinal axis of the examination table is concerned; the disadvantage consists in that the active part of the selector, i.e. that in which the radiographic film is sensitized by the X-rays, cannot be brought up to one of the ends of the examination table, because of the room required for this additional space. This defect is important, in that in some cases an examination cannot be readily accomplished and may require the patient to be moved. In the case where the dimensional increase of the selector is along an axis transversal to the examination table; the above-mentioned disadvantage no longer exists; on the other hand this dimensional increase of the selector leads to increasing to the same extent the width of the examination table.

SUMMARY OF THE INVENTION

The present invention relates to a selector, which for all the positions which it may occupy in the examination table including the endmost positions, is operational for radiography without adversely affecting the usual features such as protection of the radiographic cassette during the radioscopy sequence, the rapidity of execution and transparency to the X-rays for the radioscopic examination. This is obtained by a quite new arrangement of the selector, leading to no modification in the usual dimensions of an examination table.

The invention provides a space-saving selector, equipping an examination table of a radiological apparatus in which it is contained, movable over the whole length of this table, comprising: a cassette-carrying plate supporting a radiographic cassette, first drive means for moving said cassette-carrying plate along axes transversal to the examination table, a second plate supporting the cassette-carrying plate, second drive means for moving said second plate parallel to a longitudinal axis of the table, wherein there are further provided apertures opening at the left and right of the selector on to zones comprising protection means against X-rays; the second drive means, in a first stage, transporting the second plate outside the selector, on one side or the other thereof, so as to shelter the radiographic cassette from the X-rays and, in a second stage, re-introducing the second plate into the selector so as to place the radiographic cassette in the radiography position.

BRIEF DESCRIPTION OF THE DRAWING

The invention will be better understood from the explanations which follow given by way of example and which refer to the single accompanying FIGURE.

The FIGURE shows in a perspective view an examination table for a radiological stand, equipped with a selector in accordance with the invention.

DESCRIPTION OF THE PREFERRED EMBODIMENT

The FIGURE shows an examination table 1 of a radiological stand, equipped with a selector 2 in accordance with the invention, placed immediately under a patient-carrying panel 3. Under selector 2, a luminance amplifier 6 comprises means for manual or motor-driven movement thereof along bars 4 and 5; this movement takes place in the whole of the inner space of table 1 along an axis parallel to axis x—x, itself parallel to the longitudinal axis of said table. In the non-limiting example of this description, the luminance amplifier 6 and selector 2 are mechanically connected together for this movement; thus, selector 2 may be centered above luminance amplifier 6 in all the positions occupied by this latter from one end to the other of the table, so as to reduce the time required to go over from radioscopy to radiography.

In another version, not shown selector 2 comprises its own moving means and positioning thereof above luminance amplifier 6 is then provided by automatic working and servo-control means which the stand comprises.

An X-ray source, not shown, situated above table 1 is operatively associated alternately with the luminance amplifier 6 for the radioscopy sequences and with a radiographic cassette for the radiography sequences; this radiographic cassette, shown in the FIGURE outside selector 2, is contained therein during the radiographic sequences. The X-ray source is movable above table 1 along an axis parallel to axis x—x; it is positioned, as well as luminance amplifier 6, either by manual control by the operator, or by means of automatic working and servo-control circuits of the stand, from which the operator may take over at any time.

For radioscopy, this positioning is carried out so that an X-ray beam, emitted by said radiation source at any incidence, along an axis for example such as axis z—z, is centered on the luminance amplifier 6. This latter is previously moved parallel to an axis $z_1$—$z_1$ by lifting means which it comprises and so as to maintain during radiography the characteristics obtained in radioscopy; this movement of the luminance amplifier 6 is carried out so that its receiving plane, not visible in the drawing, occupies in selector 2 the same level as that occupied by the upper plane 37 of the radiography cassette 7, when it is contained in selector 2. During the radioscopy sequence, selector 1 must present no obstacle to the passage of the X-ray beam and this condition is achieved in the following way: on the one hand, the radiographic cassette 7, normally introduced through aperture 8 into selector 2 at the beginning of an examination is automatically transported, before the X-ray emission begins, outside selector 2 where it is sheltered from this radiation by a flexible membrane 9; on the other hand, masking flaps 17, which selector 2 comprises, movable by drive means parallel to an axis y—y transversal to table 1, are moved away from each other as much as possible.

Selector 2 comprises means cooperating with the automatic working circuits of the stand, for determining at all times, depending on the position occupied by this selector in table 1, the side through which the radiographic cassette must be removed, this side being the one opposite the end of the table which selector 2 is the nearest to. This operation is carried out as soon as the automatic working circuit receives the order to go over to a radioscopy sequence, or when selector 2 is near one end of table 1 in the vicinity of which is already located the radiographic cassette, outside said selector; in this latter case, the automatic control takes charge of the operation consisting in transporting the radiographic cassette to the other side of selector 2. This obviously causes a brief interruption of the radioscopy viewing, likely to interfere with the examination; therefore, it is generally the operator who, knowing the side towards which the examination is to be continued and before the examination begins, himself controls said transport of the radiographic cassette 7.

To this end, the selector is provided on each of its sides 27 and 11 with an aperture 12, visible in the drawing only on side 27, through which may pass a plate 13 movable by a drive means along bars 4 and 5; this plate 13 supports cassette-carrying plate 14 itself supporting the radiographic cassette 7. This latter is held on cassette-carrying plate 14 by elements 16 which clamp it and hold it as soon as it is introduced into selector 2; this latter comprises sensors cooperating with elements 16 for informing the automatic working circuits of the dimension of the radiographic cassette 7, and the relative positions of flaps 17, plate 13 and cassette-carrying plate 14. This latter is provided with drive means for moving it along axes transversal to table 1 and parallel to axis y—y in grooves 15 formed in plate 13: the movement of the cassette-carrying plate 14 allows the radiographic cassette 7 to be positioned during the radiographic sequences.

The FIGURE illustrates more especially a frequent situation in which the radioscopic examination is carried out at one end of an examination table.

In the non-limiting example of this description, it is at the left-hand side of the table 1 that this radioscopic examination is carried out and the luminance amplifier 6 and selector 2 are centered on axis z—z of the radiation beam emitted by the source located above said table; so as not to create any obstacles to the passage of the X-rays, flaps 17 of selector 2 are moved away from each other and the radiographic cassette 7, through movement of plate 13 passing through aperture 12, is transported to the right-hand side of selector 2, leaving the passage free for the X-ray beam, while allowing selector 2 to be in position for the next radiography sequence. In this position, the radiographic cassette 7 is sheltered from the X-rays by a screen presenting great opacity to X-rays and mechanical flexibility allowing it to be curved, such for example as a flexible membrane 9 formed from rubber with a high lead content. This flexible membrane 9, fixed to the side 27 of selector 2 by a bracket 18 is held tensioned by an ordinary cloth 19 to which it is firmly secured by any means, such for example as rivets 20. This cloth is itself tensioned by a device of which the ends of rollers 25 and 26 are visible on the right-hand side of the drawing, because of the presence of an aperture formed in the wall of table 1, and the equivalent of which shown on the left-hand side of this drawing, is explained in the description which follows. Side 11 of selector 2 comprises a bracket 21 similar to bracket 18, for fixing onto selector 2 a flexible membrane 10, identical to flexible membrane 9, and whose flexibility allows it to pass round roller 22, similar to roller 25; this roller 22 is fixed to table 1 by brackets 30, similar to the brackets, not shown, securing roller 25. The end of this flexible membrane is firmly secured to an ordinary cloth 23, of the same nature as cloth 19, whose other end is fixed to a roller 24, identical to roller 26; this roller 24 is secured to table 1 by means of brackets 31 similar to the brackets, not shown, securing roller 26. By means of a spring device, not shown, roller 24 exerts a constant pull on cloth 23 tending to wind it up when selector 2 approaches the left-hand end of table 1, and letting it unwind when the selector moves away therefrom, thus maintaining the flexible membrane 10 under tension. This description is also valid for the device tensioning flexible memberane 9, it being understood of course that the acting direction is opposite.

For more central positions of selector 2, flexible membranes 9 and 10 are both horizontal; if selector 2 is situated at the right-hand end of table 1, only flexible membrane 10 is horizontal, ready to shelter the radiographic cassette which, during the radioscopy, is placed at the left-hand end of the selector through movement of plate 13.

This description shows that the arrangement of the selector in accordance with the invention allows it to remain centered above a luminance amplifier 6 used for radioscopy, for all the positions which this latter is caused to occupy in the examination table, including the ends, while maintaining a radiographic cassette 7 sheltered from the X-rays, without requiring a different dimension of the examination table for protecting said radiographic cassette. This is obtained, more especially through cooperation between the flexible membranes 9 and 10 and respectively rollers 25 and 22, for swinging from a horizontal plane to a vertical plane that one of said membranes which arrives at one end of table 1, thus freeing the space required for positioning selector 2 at this end.

At the end of the radioscopy sequence, the luminance amplifier 6 frees the space which it occupies in selector 2 and the radiographic cassette 7, through movement of plate 13 is re-introduced into selector 2 where it is ready to be used. The automatic control of selector 2 combines the movements of plate 13 and cassette-carrying plate 14 with the movement of flaps 17 so as to present to the X-rays the film surface to be sensitized, in the desired format, according to a pre-established program.

With the movement of plate 13, on one side or the other of selector 2, because of the presence of apertures 12 which this latter comprises, cooperating with the flexible membrances 9 and 10, a selector in accordance with the invention may, in a first stage, free the path for the radiation beam and place a radiographic cassette 7 in a position sheltered from this X-radiation which is intended for radioscopy and, in a second stage, re-introduce this radiographic cassette into selector 2 for proceeding with the radiographic operation.

A selector in accordance with the invention may equip any radiological apparatus, whether it is tiltable or not, comprising a radiographic film, or other sensitive component, capable of being alternately subjected to sensitization and protection, and this for any position in space of a table to which it is fitted.

What is claimed is:

1. In a space-saving selector equipping an examination table of a radiological apparatus in which it is contained, movable over the whole length of said table, comprising: a cassette-carrying plate supporting a radiographic cassette, first drive means for moving said cassette-carrying plate along axes transversal to the exmination table, a second plate supporting said cassette-carrying plate, second drive means for moving said second plate parallel to a longitudinal axis of said table, there are further provided apertures opening at the right and left of the selector on to zones comprising means for protecting said radiographic cassette against X-radiation; said second drive means, in a first stage, transporting said second plate outside the selector, on one side or the other thereof, so as to place the radiographic cassette in a position sheltered from the X-rays and, in a second stage, re-introducing said second plate into the selector so as to place the radiographic cassette in the radiographic position.

2. The selector as claimed in claim 1, wherein said means for protecting against X-rays are integral with the selector on the sides thereof where said apertures are located.

3. The selector as claimed in claim 2 characterized in that said means for protecting against X-rays are formed by flexible membranes.

4. The selector as claimed in claim 1, characterized in that said means for protecting against X-rays are formed by flexible membranes.

5. The selector as claimed in claim 4, wherein said flexible membranes each comprise a means cooperating with a tensioning device for maintaining them under tension.

6. The selector as claimed in claim 5, wherein said means which said flexible membranes comprise for maintaining then tensioned are cloths.

7. The selector as claimed in claim 6, wherein said tensioning devices are formed by rollers around which said cloths wind or unwind.

8. The selector as claimed in one of claims 4, 5, 6 or 7, wherein said flexible membranes are formed by rubber with a high lead content.

9. The selector as claimed in any one of claims 3, 5, 6 or 7, wherein said flexible membranes each cooperate with a respective roller for swinging from a horizontal plane to a vertical plane.

10. The selector as in claim 9, wherein said flexible membranes are formed by rubber with a high lead content.

* * * * *